| United States Patent [19] | [11] Patent Number: 5,032,520 |
| Binns et al. | [45] Date of Patent: Jul. 16, 1991 |

[54] DNA SEQUENCES ENCODING INFECTIOUS BRONCHITIS VIRUS SPIKE PROTEIN

[75] Inventors: Matthew M. Binns; Michael E. G. Boursnell; Thomas D. K. Brown, all of Huntingdon; Fiona M. Tomley, Cambridge, all of England

[73] Assignee: National Research Development Corporation, London, England

[21] Appl. No.: 930,282

[22] PCT Filed: Mar. 27, 1986

[86] PCT No.: PCT/GB86/00181
§ 371 Date: Nov. 4, 1986
§ 102(e) Date: Nov. 4, 1986

[87] PCT Pub. No.: WO86/05806
PCT Pub. Date: Oct. 9, 1986

[30] Foreign Application Priority Data

Mar. 29, 1985 [GB] United Kingdom ............... 8508265
Jun. 20, 1985 [GB] United Kingdom ............... 8515678

[51] Int. Cl.$^5$ .................. C12N 7/01; C12N 5/10; C12N 15/50; C12N 15/86
[52] U.S. Cl. ............... 435/240.2; 435/69.1; 435/70.1; 435/91; 435/172.1; 435/172.3; 435/235.1; 435/236; 435/240.1; 435/320.1; 536/27; 935/6; 935/8; 935/9; 935/11; 935/22; 935/23; 935/32; 935/47; 935/48; 935/59; 935/60; 935/63
[58] Field of Search ............ 435/69.1, 91, 70.1, 435/172.1, 172.3, 235, 236, 240.1, 240.2, 320; 536/27; 935/6, 8, 9, 11, 22, 23, 32, 47, 48, 59, 60, 61, 63

[56] References Cited

U.S. PATENT DOCUMENTS 4,738,846  4/1988  Rose et al. ................. 424/87

OTHER PUBLICATIONS

Mackett et al., 1984, J. Virol. 49(3):857-864.
Biological Abstract 78(2):12149 Brown et al., 1984 Avian Pathology 13(1):109-118, "Confirmation of the Presence of Avian Infectious Bronchitis Virus Using Cloned DNA Complementary to the 3' Terminus of the Infectious Bronchitis Virus Genome".
Chemical Abstracts 101:144896y Genetically Engineered Vaccine Against Avian Infectious Bronchitis Virus with the Advantages of Current Live and Killed Vaccines, Cavanagh et al. 1984 In:Mod. Approaches Vaccines: Mol. Chem. Basis Virus Virulence Immunogenicity, Cold Spring Harbor Lab., N.Y. 215-218.
Chemical Abstracts 101:164558t, Sequence of the Membrane Protein Gene from Avian Coronavirus IBV. Virus Res. 1984 1(4):303-313 (Eng.).
Chemical Abstracts 102:179970r DNA Sequencing Studies of Genomic cDNA Clones of Avian Infectious Bronchitis Virus, Boursnell et al., Adv. Exp. Med. Biol. 1984, 173(Mol. Biol. Pathog. (Coronaviruses).
Boursnell et al., 1984 Gene 29:87-92.
Stern et al., 1984, J. Virol. 50:22-29.
D. Cavanagh et al., Avian Pathology 13, 573-583 (1984).

(List continued on next page.)

Primary Examiner—Richard A. Schwartz
Assistant Examiner—Richard Peet
Attorney, Agent, or Firm—Nixon & Vanderhye

[57] ABSTRACT

The problem of diagnosis and typing of infectious bronchitis virus in poultry has been solved and important progress made towards an IBV vaccine by this invention. DNA complementary to the region of genomic IBV RNA which codes for a spike protein polypeptide comprising the S1 polypeptide (containing antigenic determinants) or the S2 polypeptide (containing means for anchoring the spike protein to the viral membrane) has been made. It can be carried by a cloning vector, incorporated in a host and cloned. It can also be cloned in a poxvirus which is used to transfect mammmalian cells. Such cells express an artificial spike protein polypeptide.

13 Claims, 2 Drawing Sheets

OTHER PUBLICATIONS

D. Cavanagh, Journal of General Virology, 64, 1187–1191 (1983).
D. Cavanagh, Journal of General Virology, 64, 1787–1791 (1983).
D. Cavanagh, Journal of General Virology, 64, 2577–2583 (1983).
T. D. K. Brown et al., Virus Research, 1, 15–24 (1984).
M.E.G. Boursnell et al. Gene 29 87–92 (1984)
M.E.G. Boursnell et al. Virus Research 1, 303–313 (1984) (chem. abs. cited as U)
D. Cavanagh et al. in "Modern Approaches to Vaccines," ed. R.M. Chanack and R.G. Lerner, Cold Spring Laboratory 1984 pages 215–218
J. K. A. Cook, The Veterinary Record 112, 104–105 (1983).
J. K. A. Cook, Avian Pathology 13, 733–741 (1984).
M. M. Binns et al., J. Gen. Virol. 66, 719–726, (1985).
D. Cavanagh, Poultry International, 80–82 (Oct. 1984).
Animal Pharm. 69, 15 (Nov. 30, 1984).
Report of the Houghton Poultry Research Station 1981–1982, pub. Houghton Poultry Research Station, Houghton, Huntingdon, Cambs. UK, (1983), pp. 49 to 51.
Report of the Houghton Poultry Research Station 1983–1984, pub. Houghton Poultry Research Station, Houghton, Huntingdon, Cambs, UK (1985), pp. 48 to 50.
M. M. Binns et al., J. Virological Methods 11, 265–269 (1985).
T. D. K. Brown et al., Avian Pathology 13, 109–117 (1984).
T. D. K. Brown et al., Journal of General Virology 65, 1437–1442 (1984).
M. E. G. Boursnell et al., Journal of General virology 66, 573–580 (1985).
M. E. G. Boursnell et al., Journal of General Virology 66, 2253–2258 (1985).
I. Brierley et al., EMBO J., 6, 3779–3785 (1987).
E. G. Strauss et al., Virology 133, 92–110 (1984).
L. Yuen & B. Moss, Proc. Natl. Acad. Sci. U.S.A., 84, 6417–6421 (1987).

DNA SEQUENCES ENCODING INFECTIOUS BRONCHITIS VIRUS SPIKE PROTEIN

BACKGROUND OF THE INVENTION

1. Field of the Invention

This invention relates to the spike protein of infectious bronchitis virus (IBV) and to a recombinant DNA method for preparing it. IBV is a virus which causes respiratory disease in the fowl, and is of particular importance in relation to poultry.

2. Description of the Prior Art

IBV is a virus of the type Coronaviridae. It has a single-stranded RNA genome, approximately 20 kb in length, of positive polarity, which specifies the production of three major structural proteins: nucleocapsid protein, membrane glycoprotein, and spike glycoprotein. The spike glycoprotein is so called because it is present in the teardrop-shaped surface projections or spikes protruding from the lipid membrane of the virus. The spike protein is believed likely to be responsible for immunogenicity of the virus, partly by analogy with the spike proteins of other corona-viruses and partly by in vitro neutralisation experiments, see, for example, D. Cavanagh et al., Avian Pathology 13, 573-583 (1984). Although the term "spike protein" is used to refer to the glycoproteinaceous material of the spike, it has recently been characterised by D. Cavanagh, Journal of General Virology 64, 1187-1191; 1787-1791; and 2577-2583 (1983) as comprising two or three copies each of two glycopolypeptides, S1 (90,000 daltons) and S2 (84,000 daltons). The polypeptide components of the glycopolypeptides S1 and S2 have been estimated after enzymatic removal of oligosaccharides to have a combined molecular weight of approximately 125,000 daltons. It appears that the spike protein is attached to the viral membrane by the S2 polypeptide.

The genomic organisation of the IBV viral proteins is summarised in, for example, T. D. K. Brown and M. E. G. Boursnell, Virus Research 1, 15-24 (1984). Briefly, six polyadenlyated IBV viral mRNA species (A to F) have been detected in infected cells. mRNA A is the smallest and mRNA F is of genome length. These mRNAs form a so-called 'nested' or 3' co-terminal set. The nested mRNAs A to E have sizes approximately 2, 2.4, 3.4, 4.1 and 7.8 kb, as estimated from formaldehyde-agarose gel electrophoresis. They are shown in the accompanying drawing. Evidence from translation studies in vitro suggests that mRNAs A, C and E are each translated to give a corresponding major polypeptide. Thus, mRNA A codes for the nucleocapsid polypeptide, mRNA C for the membrane polypeptide and mRNA E for the precursor of the spike protein. In connection with mRNA E D. F. Stern and B. M. Sefton, Journal of Virology 50, 22-29 (1984) found that this mRNA specified production of the spike protein precursor in an in vitro translation. The sizes of the translation products are consistent with the coding capacity being present at the 5' end of each mRNA, but not present in the next smallest mRNA. In other words, the coding portion is within the "unique" region, i.e. the region of 'non-overlap' between successive RNAs of the set. U.v. inactivation studies have demonstrated that the subgenomic mRNAs are not produced by processing of larger RNA species, but are synthesised independently.

DNA complementary to IBV RNA (hereinafter referred to as 'cDNA') has been obtained for the Beaudette strain of IBV, as two fragments, together encompassing the first 3.3 kb of RNA from the 3' end, extending nearly to the 5' end of mRNA C. The fragments were inserted in plasmids and cloned in E. coli. They are described as C5.136 and C5.322 in T. D. K. Brown and M. E. G. Boursnell, supra, C5.136 being that running from nucleotides 1000 to 3300 approximately. Sequence information on C5.136 from nucleotides 1630 to 2400 approximately and the cloning of cDNA for IBV Beaudette strain including mRNA B and the 5' region of mRNA A have been described by M. E. G. Boursnell and T. D. K. Brown, Gene 29, 87-92 (1984). Futher C5.136 sequence from nucleotides 2200 to 3400 approximately has been published by M. E. G. Boursnell, T. D. K. Brown and M. M. Binns, Virus Research 1, 303-313 (1984).

In the paper 'Genetically Engineered Vaccine against Avian Infectious Bronchitis Virus with the Advantages of Current Live and Killed VAccines', by D. Cavanagh and the present inventors (M. M. Binns, M. E. G. Boursnell and T. D. K. Brown) in 'Modern Approaches to Vaccines', Cold Spring Harbor Laboratory, New York 1984, pages 215-218, it was announced that an oligonucleotide primer had been made and was currently being used to extend the C5.136 DNA so as to encompass the spike protein precursor gene. The oligonucleotide primer was described as corresponding to a sequence of 13 nucleotides approximately 150 bases in from the 5' terminus of C5.136. The nature and exact location of the oligonucleotide in the C5.136 cDNA sequence in the region from nucleotides 2400 to 3300 (the 5' terminus) have not been disclosed by these workers in any way, in writing or orally.

SUMMARY OF THE INVENTION

The present invention arises out of the research projected in broad outline above in 'Modern Approaches to Vaccines'. cDNA has been prepared by the primer method outlined above and within this cDNA sequences coding for the spike protein precursor (S) as well as sequences coding specifically for the S1 and S2 polypeptides have been identified. Cloned S, S1 and S2 DNA are starting materials for preparation of artificial polypeptides useful in a vaccine against IBV. Additionally, such DNA can be labelled to provide probes diagnostically useful in identifying IBV infections or in typing an infecting virus.

The research described has been carried out on three strains of IBV namely the Beaudette, M41 and 6/82 strains of IBV, but it is expected that other IBV serotypes and strains will exhibit a high degree of homology with one or more of these in respect of the spike protein precursor-coding cDNA.

According to an important feature of the invention there is provided a DNA molecule which codes for an IBV spike protein polypeptide comprising (consisting of or including) the S1 or S2 polypeptide. Such DNA is conveniently referred to as "spike DNA" for brevity. It includes DNA coding for the spike protein precursor. Preferably there is at least 80%, more preferably at least 90%, amino acid sequence homology between the sequence coded for and the amino acid sequence of the corresponding polypeptide of the IBV Beaudette, M41 or 6/82 strain.

The invention includes specifically a DNA molecule which codes substantially only for any of (1) the spike protein precursor, (2) the S1 signal plus the S1 polypeptide, (3) the S1 polypeptide and (4) the S1 plus the S2 polypeptides, each said coding being to an extent of at least 80%, preferably at least 90%, amino acid sequence homology between the sequence coded for and the amino acid sequence of the corresponding protein of the IBV Beaudette M41, or 6/82 strain.

According to a preferred aspect of the invention there is included spike DNA as defined above which also shows at least 75%, preferably at least 80%, more preferably at least 90%, and most preferably at least 95%, nucleotide sequence homology with the corresponding nucleotide sequence of the IBV Beaudette, M41 or 6/82 strain.

In referring to DNA defined as coding substantially only for the various polypeptides it will be appreciated that it is intended not to exclude flanking DNA sequences, which may be, for example, cDNA to flanking sequences in the IBV RNA genome or may be foreign sequences derived from other genes. Also, it is not intended that the S1 DNA should necessarily code for amino acids extending right up to each terminus. It is expected that it will be possible to obtain expression of S1 cDNA lacking say, up to 5 or even 10 of the amino acids (30 nucleotides) at either terminus.

The invention also includes a vector containing the above-defined IBV spike DNA, including a cloning vector such as a plasmid or phage or an expression vector, preferably a poxvirus vector, and a host containing the vector. Mammalian cells containing the IBV spike DNA, whether as naked DNA or contained in a vector, are also included. Further, the invention includes artificial spike protein polypeptide and its expression from mammalian cells.

DESCRIPTION OF THE PREFERRED EMBODIMENTS

Figure 1:
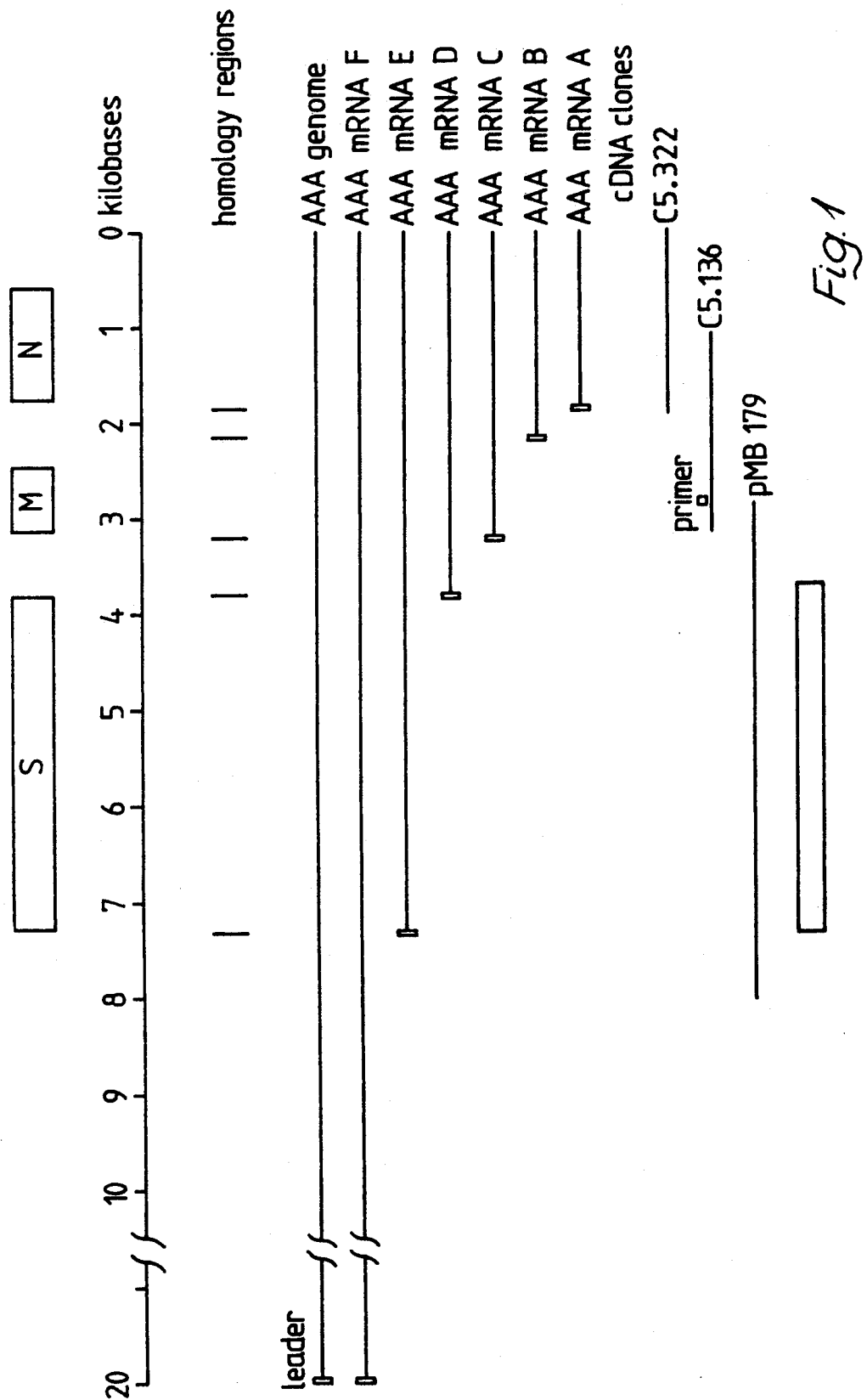
FIG. 1 is a map of genomic and messenger RNA or IBV Beaudette strain showing cDNA clones and a primer used in obtaining the spike DNA of this invention.

Sequence formula (1) below shows the complete nucleotide sequence of a cDNA molecule of the invention obtained from IBV genomic RNA Beaudette strain. To appreciate more fully the correspondence of this DNA with the genomic and mRNA it is useful first to refer to FIG. 1 of the drawing which shows the nested set of mRNAs. Each mRNA has a "leader" sequence at its 5'-end, this being shown in the drawing as a small rectangle. The leader sequence does not appear in the corresponding part of the genomic RNA, but only at the 5'-end of the whole genome. For convenience, we shall refer to the mRNA/genomic RNA common sequence as the "body" of the mRNA. The IBV spike protein precursor is located substantially wholly within that portion of mRNA E which extends 5'-wards beyond the 5' terminus of the body of mRNA D on the genome, i.e. from approximately nucleotides 4000 to 7500 of the genome. Sequence formula (1) shows a cDNA extending from the 5' terminus of the body of the mRNA E on the genome at about nucleotide 39 to the two stop codons at nucleotides 3587 to 3592. The start codon at nucleotides 101 to 103 begins an open reading frame of 3486 nucleotides coding for 1162 amino acids, indicating a non-glycosylated protein of molecular mass about 127,000 daltons.

```
GATTTGAGATTGAAAGCAACGCCAGTTGTTAATTTGAAAACTGAACAAAAGACAGACTTA           (1)
      10        20        30        40        50        60

M  L  V  T  P  L  L
GTCTTTAATTTAATTAAGTGTGGTAAGTTACTGGTAAGAGATGTTGGTAACACCTCTTTT
      70        80        90       100       110       120

L  V  T  L  L  C  A  L  C  S  A  V  L  Y  D  S  S  S  Y  V
ACTAGTGACTCTTTTGTGTGCACTATGTAGTGCTGTTTTGTATGACAGTAGTTCTTACGT
     130       140       150       160       170       180

Y  Y  Y  Q  S  A  F  R  P  P  S  G  W  H  L  Q  G  G  A  Y
TTACTACTACCAAAGTGCCTTCAGACCACCTAGTGGTTGGCATTTACAAGGGGGTGCTTA
     190       200       210       220       230       240

A  V  V  N  I  S  S  E  F  N  N  A  G  S  S  S  G  C  T  V
TGCGGTAGTTAACATTTCTAGCGAATTTAATAATGCAGGCTCTTCATCAGGGTGTACTGT
     250       260       270       280       290       300

G  I  I  H  G  G  R  V  V  N  A  S  S  I  A  M  T  A  P  S
TGGTATTATTCATGGTGGTCGTGTTGTTAATGCTTCTTCTATAGCTATGACGGCACCGTC
     310       320       330       340       350       360

S  G  M  A  W  S  S  S  Q  F  C  T  A  H  C  N  F  S  D  T
ATCAGGTATGGCTTGGTCTAGCAGTCAGTTTTGTACTGCACACTGTAATTTTTCAGATAC
     370       380       390       400       410       420

T  V  F  V  T  H  C  Y  K  H  G  G  C  P  L  T  G  M  L  Q
TACAGTGTTTGTTACACATTGTTATAAACATGGTGGGTGTCCTTTAACTGGCATGCTTCA
     430       440       450       460       470       480
```

-continued

```
          Q   N   L   I   R   V   S   A   M   K   N   G   Q   L   F   Y   N   L   T   V
        ACAGAATCTTATACGTGTTTCTGCTATGAAAAATGGCCAGCTTTTCTATAATTTAACAGT
            490         500         510         520         530         540

S   V   A   K   Y   P   T   F   R   S   F   Q   C   V   N   N   L   T   S   V
        TAGTGTAGCTAAGTACCCTACTTTTAGATCATTTCAGTGTGTTAATAATTTAACATCCGT
            550         560         570         580         590         600

Y   L   N   G   D   L   V   Y   T   S   N   E   T   I   D   V   T   S   A   G
        ATATTTAAATGGTGATCTTGTTTACACCTCTAATGAGACCATAGATGTTACATCTGCAGG
            610         620         630         640         650         660

V   Y   F   K   A   G   G   P   I   T   Y   K   V   M   R   E   V   K   A   L
        TGTTTATTTTAAAGCTGGTGGACCTATAACTTATAAAGTTATGAGAGAAGTTAAAGCCCT
            670         680         690         700         710         720

A   Y   F   V   N   G   T   A   Q   D   V   I   L   C   D   G   S   P   R   G
        GGCTTATTTTGTTAATGGTACTGCACAAGATGTTATTTTGTGTGATGGATCACCTAGAGG
            730         740         750         760         770         780

L   L   A   C   Q   Y   N   T   G   N   F   S   D   G   F   Y   P   F   T   N
        CTTGTTAGCATGCCAGTATAATACTGGCAATTTTTCAGATGGCTTTTATCCTTTTACCAA
            790         800         810         820         830         840

S   S   L   V   K   Q   K   F   I   V   Y   R   E   N   S   V   N   T   T   C
        TAGTAGTTTAGTTAAGCAGAAGTTTATTGTCTATCGTGAAAATAGTGTTAATACTACTTG
            850         860         870         880         890         900

T   L   H   N   F   I   F   H   N   E   T   G   A   N   P   N   P   S   G   V
        TACGTTACACAATTTCATTTTTCATAATGAGACTGGCGCCAACCCTAATCCTAGTGGTGT
            910         920         930         940         950         960

Q   N   I   Q   T   Y   Q   T   K   T   A   Q   S   G   Y   Y   N   F   N   F
        TCAGAATATTCAAACTTACCAAACAAAAACAGCTCAGAGTGGTTATTATAATTTTAATTT
            970         980         990         1000        1010        1020

S   F   L   S   S   F   V   Y   K   E   S   N   F   M   Y   G   S   Y   H   P
        TTCCTTTCTGAGTAGTTTTGTTTATAAGGAGTCTAATTTTATGTATGGATCTTATCACCC
            1030        1040        1050        1060        1070        1080

S   C   K   F   R   L   E   T   I   N   N   G   L   W   F   N   S   L   S   V
        AAGTTGTAAATTTAGACTAGAAACTATTAATAATGGCTTGTGGTTTAATTCACTTTCAGT
            1090        1100        1110        1120        1130        1140

S   I   A   Y   G   P   L   Q   G   G   C   K   Q   S   V   F   K   G   R   A
        TTCAATTGCTTACGGTCCTCTTCAAGGTGGTTGCAAGCAATCTGTCTTTAAAGGTAGAGC
            1150        1160        1170        1180        1190        1200

T   C   C   Y   A   Y   S   Y   G   G   P   S   L   C   K   G   V   Y   S   G
        AACTTGTTGTTATGCTTATTCATATGGAGGTCCTTCGCTGTGTAAAGGTGTTTATTCAGG
            1210        1220        1230        1240        1250        1260

E   L   D   H   N   F   E   C   G   L   L   V   Y   V   T   K   S   G   G   S
        TGAGTTAGATCATAATTTTGAATGTGGACTGTTAGTTTATGTTACTAAGAGCGGTGGCTC
            1270        1280        1290        1300        1310        1320

R   I   Q   T   A   T   E   P   P   V   I   T   Q   N   N   Y   N   N   I   T
        TCGTATACAAACAGCCACTGAACCGCCAGTTATAACTCAAAACAATTATAATAATATTAC
            1330        1340        1350        1360        1370        1380

L   N   T   C   V   D   Y   N   I   Y   G   R   T   G   Q   G   F   I   T   N
        TTTAAATACTTGTGTTGATTATAATATATATGGCAGAACTGGCCAAGGTTTTATTACTAA
            1390        1400        1410        1420        1430        1440

V   T   D   S   A   V   S   Y   N   Y   L   A   D   A   G   L   A   I   L   D
        TGTGACCGACTCAGCTGTTAGTTATAATTATCTAGCAGACGCAGGTTTGGCTATTTTAGA
            1450        1460        1470        1480        1490        1500

T   S   G   S   I   D   I   F   V   V   Q   G   E   Y   G   L   N   Y   Y   K
        TACATCTGGTTCCATAGACATCTTTGTTGTACAAGGTGAATATGGTCTTAATTATTATAA
            1510        1520        1530        1540        1550        1560
```

-continued

```
      V   N   P   C   E   D   V   N   Q   Q   F   V   V   S   G   G   K   L   V   G
      GGTTAACCCTTGCGAAGATGTCAACCAGCAGTTTGTAGTTTCTGGTGGTAAATTAGTAGG
         1570        1580        1590        1600        1610        1620

I   L   T   S   R   N   E   T   G   S   Q   L   L   E   N   Q   F   Y   I   K
      TATTCTTACTTCACGTAATGAGACTGGTTCTCAGCTTCTTGAGAACCAGTTTTACATCAA
         1630        1640        1650        1660        1670        1680

↓
      I   T   N   G   T   R   R   F   R   R   S   I   T   E   N   V   A   N   C   P
      AATCACTAATGGAACACGTCGTTTTAGACGTTCTATTACTGAAAATGTTGCAAATTGCCC
         1690        1700        1710        1720        1730        1740

Y   V   S   Y   G   K   F   C   I   K   P   D   G   S   I   A   T   I   V   P
      TTATGTTAGTTATGGTAAGTTTTGTATAAAACCTGATGGCTCAATTGCCACAATAGTACC
         1750        1760        1770        1780        1790        1800

K   Q   L   E   Q   F   V   A   P   L   F   N   V   T   E   N   V   L   I   P
      AAAACAATTGGAACAGTTTGTGGCACCTTTATTTAATGTTACTGAAAATGTGCTCATACC
         1810        1820        1830        1840        1850        1860

N   S   F   N   L   T   V   T   D   E   Y   I   Q   T   R   M   D   K   V   Q
      TAACAGTTTCAACTTAACTGTTACAGATGAGTACATACAAACGCGTATGGATAAGGTCCA
         1870        1880        1890        1900        1910        1920

I   N   C   L   Q   Y   V   C   G   S   S   L   D   C   R   K   L   F   Q   Q
      AATTAATTGCCTGCAGTATGTTTGTGGCAGTTCTCTGGATTGTAGAAAGTTGTTTCAACA
         1930        1940        1950        1960        1970        1980

Y   G   P   V   C   D   N   I   L   S   V   V   N   S   V   G   Q   K   E   D
      ATATGGGCCTGTTTGCGACAACATATTGTCTGTAGTAAATAGTGTTGGTCAAAAAGAAGA
         1990        2000        2010        2020        2030        2040

M   E   L   L   N   F   Y   S   S   T   K   P   A   G   F   N   T   P   V   L
      TATGGAACTTTTGAATTTCTATTCTTCTACTAAACCGGCTGGTTTTAATACACCAGTTCT
         2050        2060        2070        2080        2090        2100

S   N   V   S   T   G   E   F   N   I   S   L   L   L   T   N   P   S   S   R
      TAGTAATGTTAGCACTGGTGAGTTTAATATTTCTCTTCTGTTAACAAATCCTAGTAGTCG
         2110        2120        2130        2140        2150        2160

R   K   R   S   L   I   E   D   L   L   F   T   S   V   E   S   V   G   L   P
      TAGAAAGCGTTCTCTTATTGAAGACCTTCTATTTACAAGCGTTGAATCTGTTGGACTACC
         2170        2180        2190        2200        2210        2220

T   N   D   A   Y   K   N   C   T   A   G   P   L   G   F   F   K   D   L   A
      AACAAATGACGCATATAAAAATTGCACTGCAGGACCTTTAGGCTTTTTTAAGGACCTTGC
         2230        2240        2250        2260        2270        2280

C   A   R   E   Y   N   G   L   L   V   L   P   P   I   I   T   A   E   M   Q
      GTGTGCTCGTGAATATAATGGTTTGCTTGTGTTGCCTCCTATCATAACAGCAGAAATGCA
         2290        2300        2310        2320        2330        2340

A   L   Y   T   S   S   L   V   A   S   M   A   F   G   G   I   T   A   A   G
      AGCTTTGTATACTAGTTCTCTAGTAGCTTCTATGGCTTTTGGTGGTATTACTGCAGCTGG
         2350        2360        2370        2380        2390        2400

A   I   P   F   A   T   Q   L   Q   A   R   I   N   H   L   G   I   T   Q   S
      TGCTATACCTTTTGCCACACAACTGCAGGCTAGAATTAATCACTTGGGTATTACCCAGTC
         2410        2420        2430        2440        2450        2460

L   L   L   K   N   Q   E   K   I   A   A   S   F   N   K   A   I   G   H   M
      ACTTTTGTTGAAGAATCAAGAAAAAATTGCTGCTTCCTTTAATAAGGCCATTGGTCATAT
         2470        2480        2490        2500        2510        2520

Q   E   G   F   R   S   T   S   L   A   L   Q   Q   I   Q   D   V   V   S   K
      GCAGGAAGGTTTTAGAAGTACATCTCTAGCATTACAACAAATTCAAGATGTTGTTAGTAA
         2530        2540        2550        2560        2570        2580

Q   S   A   I   L   T   E   T   M   A   S   L   N   K   N   F   G   A   I   S
      ACAGAGTGCTATTCTTACTGAGACTATGGCATCACTTAATAAAAATTTTGGTGCTATTTC
         2590        2600        2610        2620        2630        2640
```

-continued

```
      S   V   I   Q   E   I   Y   Q   Q   F   D   A   I   Q   A   N   A   Q   V   D
    TTCTGTGATTCAAGAAATCTACCAGCAATTTGACGCCATACAAGCAAATGCTCAAGTGGA
       2650      2660      2670      2680      2690      2700

R   L   I   T   G   R   L   S   S   L   S   V   L   A   S   A   K   Q   A   E
    TCGTCTTATAACTGGTAGATTGTCATCACTTTCTGTTTTAGCATCTGCTAAGCAGGCGGA
       2710      2720      2730      2740      2750      2760

Y   I   R   V   S   Q   Q   R   E   L   A   T   Q   K   I   N   E   C   V   K
    GTATATTAGAGTGTCACAACAGCGTGAGTTAGCTACTCAGAAAATTAATGAGTGTGTTAA
       2770      2780      2790      2800      2810      2820

S   Q   S   I   R   Y   S   F   C   G   N   G   R   H   V   L   T   I   P   Q
    GTCACAGTCTATTAGGTACTCCTTTTGTGGTAATGGACGACATGTTCTAACCATACCGCA
       2830      2840      2850      2860      2870      2880

N   A   P   N   G   I   V   F   I   H   F   S   Y   T   P   D   S   F   V   N
    AAATGCACCTAATGGTATAGTGTTTATACACTTTTCTTATACTCCAGATAGTTTTGTTAA
       2890      2900      2910      2920      2930      2940

V   T   A   I   V   G   F   C   V   K   P   A   N   A   S   Q   Y   A   I   V
    TGTTACTGCAATAGTGGGTTTTTGTGTAAAGCCAGCTAATGCTAGTCAGTATGCAATAGT
       2950      2960      2970      2980      2990      3000

P   A   N   G   R   G   I   F   I   Q   V   N   G   S   Y   Y   I   T   A   R
    GCCCGCTAATGGTAGGGGTATTTTTATACAAGTTAATGGTAGTTACTACATCACTGCACG
       3010      3020      3030      3040      3050      3060

D   M   Y   M   P   R   A   I   T   A   G   D   V   V   T   L   T   S   C   Q
    AGATATGTATATGCCAAGAGCTATTACTGCAGGAGATGTAGTTACGCTTACTTCTTGTCA
       3070      3080      3090      3100      3110      3120

A   N   Y   V   S   V   N   K   T   V   I   T   T   F   V   D   N   D   D   F
    AGCAAATTATGTAAGTGTAAATAAGACCGTCATTACTACATTCGTAGACAATGATGATTT
       3130      3140      3150      3160      3170      3180

D   F   N   D   E   L   S   K   W   W   N   D   T   K   H   E   L   P   D   F
    TGATTTTAATGACGAATTGTCAAAATGGTGGAATGATACTAAGCATGAGCTACCAGACTT
       3190      3200      3210      3220      3230      3240

D   K   F   N   Y   T   V   P   I   L   D   I   D   S   E   I   D   R   I   Q
    TGACAAATTCAATTACACAGTACCTATACTTGACATTGATAGTGAAATTGATCGTATTCA
       3250      3260      3270      3280      3290      3300

G   V   I   Q   G   L   N   D   S   L   I   D   L   E   K   L   S   I   L   K
    AGGCGTTATACAGGGTCTTAATGACTCTCTAATAGACCTTGAAAAACTTTCAATACTCAA
       3310      3320      3330      3340      3350      3360

T   Y   I   K   W   P   W   Y   V   W   L   A   I   A   F   A   T   I   I   F
    AACTTATATTAAGTGGCCTTGGTATGTGTGGTTAGCCATAGCTTTTGCCACTATTATCTT
       3370      3380      3390      3400      3410      3420

I   L   I   L   G   W   V   F   F   M   T   G   N   A   R   E   G   C   C   G   C
    CATCTTAATACTAGGATGGGTTTTCTTCATGACTGGTTGTTGTGGTTGTTGTTGTGGATG
       3430      3440      3450      3460      3470      3480

F   G   I   M   P   L   M   S   K   C   G   K   K   S   S   Y   Y   T   T   F
    CTTTGGCATTATGCCTCTAATGAGTAAGTGTGGTAAGAAATCTTCTTATTACACGACTTT
       3490      3500      3510      3520      3530      3540

D   N   D   V   V   T   E   Q   Y   R   P   K   K   S   V   *   *
    TGATAACGATGTGGTAACTGAACAATACAGACCTAAAAAGTCTGTTTGATGATCCAAAGT
       3550      3560      3570      3580      3590      3600

CCCACGTCCTTCCTAATAGTATTAATTCTTCTTTGGTGTAAACTT
       3610      3620      3630      3640
```

This molecular weight is close to that estimated for the polypeptide components S1 and S2. In vitro translation of mRNA E had indicated that the nonglycosylated spike precursor protein had a molecular weight of 110,000 daltons while estimates of the combined molecular weight of S1 and S2 after the removal of oligosaccharides by endoglycosidase H were 115,000 and 125,000.

The cDNA contains sequences AACTGAACAAAA towards the 5' end and AACTGAACAATA towards the 3' end, underlined in formula (1). From their high homology with sequence, referred to in the drawing as 'homology regions', which have previously been found at the 5' ends of the bodies of IBV mRNAs A, B and C and from mRNA length measurements it appears that these sequences represent approximately the position of the 5' ends of the bodies of mRNAs E and D. Surprisingly, the coding sequences for the spike protein gene are not completely contained within the 'unique' region of mRNA E but extend for approximately 32 bases beyond the predicted 5' terminus of the body of mRNA D.

The spike protein precursor cDNA can be regarded as all that cDNA present in the open reading frame, including a signal region from nucleotides 101 to 154 shown boxed, an S1 polypeptide-coding region from nucleotides 155 to 1696 and an S2 polypeptide-coding region from 1712 to 3586. The S1 and S2 polypeptide-coding regions are joined by a sequence from 1697 to 1711 coding for the amino acids RRFRR. This sequence of amino acids present in the precursor polypeptide is believed to be cleaved during post-translation processing. The 5' end of the S2 sequence has been determined by amino acid sequencing and is shown arrowed at nucleotide 1712. Other features of the formula (1) sequence are referred to in the Examples hereinafter.

cDNA for spike protein polypeptides of the well known strain M41 and the strain 6/82 has been prepared using Beaudette strain RNA or cDNA as a hybridisation probe or to make a primer. Strain 6/82 was isolated in 1982 by Jane K. A. Cook, Vet. Record 112, 104–105 (1983) and is available without restriction from Houghton Poultry Research Station, Houghton, Huntingdon, Cambridgeshire PE7 2DA, England, subject, of course, to compliance with legal regulations. Strain 6/82, which is isolate No. 2 of J. K. A. Cook, Avian Pathology 13, 733–741 (1984), exhibits cross-neutralisation reactions with Dutch serotypes.

Sequence formula (2) below compares the spike DNA sequences for Beaudette, M41, and 6/82, the 5'-end of which is the same for Beaudette as in sequence formula (1). There is a region of relatively high heterology between nucleotides 449 to 499, including particularly 458 to 463 for 6/82, which has six extra nucleotides not present in M41 or Beaudette. The numbering system was therefore adjusted to align with 6/82, with the result that the Beaudette nucleotides after 458 are six numbers on from those in sequence formula (1). Overall, the three sequences show a high degree of homology. An analysis of M41 and Beaudette showed 70/3510 nucleotide changes resulting in 43/1139 amino acid changes. Strain 6/82 shows a lower degree of homology with M41 or Beaudette.

```
               10         20         30         40         50
BEAU    GATTTGAGATTGAAAGCAACGCCAGTTGTTAATTTGAAAACTGAACAAAA 60         70         80         90        100
BEAU    GACAGACTTAGTCTTTAATTTAATTAAGTGTGGTAAGTTACTGGTAAGAG 110        120        130        140        150
M41                                                ACTATGTAG
BEAU    ATGTTGGTAACACCTCTTTTACTAGTGACTCTTTTGTGTGCACTATGTAG 160        170        180        190        200
M41     TGCTGCTTTGTATGACAGTAGTTCTTACGTTTACTACTACCAAAGTGCCT
BEAU    TGCTGTTTTGTATGACAGTAGTTCTTACGTTTACTACTACCAAAGTGCCT 210        220        230        240        250
M41     TTAGACCACCTAATGGTTGGCATTTACACGGGGGTGCTTATGCGGTAGTT
BEAU    TCAGACCACCTAGTGGTTGGCATTTACAAGGGGGTGCTTATGCGGTAGTT 260        270        280        290        300
M41     AATATTTCTAGCGAATCTAATAATGCAGGCTCTTCACCTGGGTGTATTGT
BEAU    AACATTTCTAGCGAATTTAATAATGCAGGCTCTTCATCAGGGTGTACTGT 310        320        330        340        350
M41     TGGTACTATTCATGGTGGTCGTGTTGTTAATGCTTCTTCTATAGCTATGA
BEAU    TGGTATTATTCATGGTGGTCGTGTTGTTAATGCTTCTTCTATAGCTATGA 360        370        380        390        400
6/82                                                 GTACGGCT
M41     CGGCACCGTCATCAGGTATGGCTTGGTCTAGCAGTCAGTTTTGTACTGCA
BEAU    CGGCACCGTCATCAGGTATGGCTTGGTCTAGCAGTCAGTTTTGTACTGCA 410        420        430        440        450
6/82    CACTGCAATTTTACTGATTTTGTAGTATTTGTTACACATTGCTATAAAAG
M41     CACTGTAACTTTTCAGATACTACAGTGTTTGTTACACATTGTTATAAATA
BEAU    CACTGTAATTTTTCAGATACTACAGTGTTTGTTACACATTGTTATAAACA 460        470        480        490        500
6/82    TGGTCATGGTTCATGTCCTTTAACAGGTCTGATTCCACAGAATCATATTC
M41     TGATGGG------TGTCCTATAACTGGCATGCGTCAAAAGAATTTTTTAC
BEAU    TGGTGGG------TGTCCTTTAACTGGCATGCTTCAACAGAATCTTATAC 510        520        530        540        550
6/82    GTATTTCTGCTATGAAAAATAGCAGTTTGTTTTATAACTTAACAGTTGCT
M41     GTGTTTCTGCTATGAAAAATGGCCAGCTTTTCTATAATTTAACAGTTAGT
BEAU    GTGTTTCTGCTATGAAAAATGGCCAGCTTTTCTATAATTTAACAGTTAGT 560        570        580        590        600
6/82    GTGACTAAATATCCTAGATTTAAGTCGCTTCAGTGTGTTAATAATATGAC
M41     GTAGCTAAGTACCCTACTTTTAAATCATTTCAGTGTGTTAATAATTTAAC
```

-continued

BEAU GTAGCTAAGTACCCTACTTTTAGATCATTTCAGTGTGTTAATAATTTAAC

```
            610       620       630       640       650
6/82  ATCTGTATACCTAAATGGCGATCTCGTTTTTACTTCTAACGAGACTAAAG
M41   ATCCGTATATTTAAATGGTGATCTTGTTTACACCTCTAATGAGACCACAG
BEAU  ATCCGTATATTTAAATGGTGATCTTGTTTACACCTCTAATGAGACCATAG 660       670       680       690       700
6/82  ATGTTAGTGCTGCAG
M41   ATGTTACATCTGCAGGTGTTTATTTTAAAGCTGGTGGACCTATAACTTAT
BEAU  ATGTTACATCTGCAGGTGTTTATTTTAAAGCTGGTGGACCTATAACTTAT 710       720       730       740       750
M41   AAAGTTATGAGAGAAGTTAAAGCCCTGGCTTATTTTGTTAATGGTACTGC
BEAU  AAAGTTATGAGAGAAGTTAAAGCCCTGGCTTATTTTGTTAATGGTACTGC 760       770       780       790       800
M41   ACAAGATGTTATTTTGTGTGATGGATCACCTAGAGGCTTGTTAGCATGCC
BEAU  ACAAGATGTTATTTTGTGTGATGGATCACCTAGAGGCTTGTTAGCATGCC 810       820       830       840       850
6/82   GTATAATACTGGTAATTTTTCAGATGGCTTTTATCCTTTTACTAATAGT
M41   AGTATAATACTGGCAATTTTTCAGATGGCTTTTATCCTTTTATTAATAGT
BEAU  AGTATAATACTGGCAATTTTTCAGATGGCTTTTATCCTTTTACTAATAGT 860       870       880       890       900
6/82  AGTTTAGTTAAGGAAAAGTTTATTGTTTATCGTGAAAGTAGTGTTAACAC
M41   AGTTTAGTTAAGCAGAAGTTTATTGTCTATCGTGAAAATAGTGTTAATAC
BEAU  AGTTTAGTTAAGCAGAAGTTTATTGTCTATCGTGAAAATAGTGTTAATAC 910       920       930       940       950
6/82  TACTTTGGAGTTAACTAATTTCACTTTTTCTAATGTAAGTAATGCTACCC
M41   TACTTTTACGTTACACAATTTCACTTTTCATAATGAGACTGGCGCCAACC
BEAU  TACTTGTACGTTACACAATTTCATTTTTCATAATGAGACTGGCGCCAACC 960       970       980       990       1000
6/82  CTAACACAGGGGGTGTCCAGACCATTCAATTATATCAAACCATCACGGCT
M41   CTAATCCTAGTGGTGTTCAGAATATTCAAACTTACCAAACACAAACAGCT
BEAU  CTAATCCTAGTGGTGTTCAGAATATTCAAACTTACCAAACAAAAACAGCT 1010      1020      1030      1040      1050
6/82  CAGAGTGGTTATTATAATCTTAATTTCTCCTTTCTGAGTAGTTTTATTTA
M41   CAGAGTGGTTATTATAATTTTAATTTTTCCTTTCTGAGTAGTTTTGTTTA
BEAU  CAGAGTGGTTATTATAATTTTAATTTTTCCTTTCTGAGTAGTTTTGTTTA 1060      1070      1080      1090      1100
6/82  TAAGGCGTCTGATTATATGTATGGGTCTTACCACCC
M41   TAAGGAGTCTAATTTTATGTATGGATCTTATCACCCAAGTTGTAATTTTA
BEAU  TAAGGAGTCTAATTTTATGTATGGATCTTATCACCCAAGTTGTAAATTTA 1110      1120      1130      1140      1150
M41   GACTAGAAACTATTAATAATGGCTTGTGGTTTAATTCACTTTCAGTTTCA
BEAU  GACTAGAAACTATTAATAATGGCTTGTGGTTTAATTCACTTTCAGTTTCA 1160      1170      1180      1190      1200
M41   ATTGCTTACGGTCCTCTTCAAGGTGGTTGCAAGCAATCTGTCTTTAGTGG
BEAU  ATTGCTTACGGTCCTCTTCAAGGTGGTTGCAAGCAATCTGTCTTTAAAGG 1210      1220      1230      1240      1250
M41   TAGAGCAACTTGTTGTTATGCTTATTCATATGGAGGTCCTTCGCTGTGTA
BEAU  TAGAGCAACTTGTTGTTATGCTTATTCATATGGAGGTCCTTCGCTGTGTA 1260      1270      1280      1290      1300
M41   AAGGTGTTTATTCAGGTGAGTTAGATCTTAATTTTGAATGTGGACTGTTA
BEAU  AAGGTGTTTATTCAGGTGAGTTAGATCATAATTTTGAATGTGGACTGTTA 1310      1320      1330      1340      1350
M41   GTTTATGTTACTAAGAGCGGTGGCTCTCGTATACAAACAGCCACTGAACC
BEAU  GTTTATGTTACTAAGAGCGGTGGCTCTCGTATACAAACAGCCACTGAACC 1360      1370      1380      1390      1400
M41   GCCAGTTATAACTCGACACAATTATAATAATATTACTTTTAAATACTTGTG
BEAU  GCCAGTTATAACTCAAAACAATTATAATAATATTACTTTTAAATACTTGTG 1410      1420      1430      1440      1450
M41   TTGATTATAATATATATGGCAGAACTGGCCAAGGTTTTATTACTAATGTA
BEAU  TTGATTATAATATATATGGCAGAACTGGCCAAGGTTTTATTACTAATGTG 1460      1470      1480      1490      1500
M41   ACCGACTCAGCTGTTAGTTATAATTATCTAGCAGACGCAGGTTTGGCTAT
BEAU  ACCGACTCAGCTGTTAGTTATAATTATCTAGCAGACGCAGGTTTGGCTAT
```

```
              1510        1520        1530        1540        1550
6/82                                                       GGTGAATATG
M41    TTTAGATACATCTGGTTCCATAGACATCTTTGTTGTACAAGGTGAATATG
BEAU   TTTAGATACATCTGGTTCCATAGACATCTTTGTTGTACAAGGTGAATATG 1560        1570        1580        1590        1600
6/82   GTCTTAATTATTATAAAGTTAACCCTTGTGAGGATGTTAATCAGCAGTTT
M41    GTCTTACTTATTATAAGGTTAACCCTTGCGAAGATGTCAACCAGCAGTTT
BEAU   GTCTTAATTATTATAAGGTTAACCCTTGCGAAGATGTCAACCAGCAGTTT 1610        1620        1630        1640        1650
6/82   GTAGTTTCTGGTGGTAAATTAGTAGGTATTCTTACGTCACGTAATGAGAC
M41    GTAGTTTCTGGTGGTAAATTAGTAGGTATTCTTACTTCACGTAATGAGAC
BEAU   GTAGTTTCTGGTGGTAAATTAGTAGGTATTCTTACTTCACGTAATGAGAC 1660        1670        1680        1690        1700
6/82   TGGCTCGCAGCCTCTTGAAAACCAGTTCTATATTAAAATCATTAATGGAA
M41    TGGTTCTCAGCTTCTTGAGAACCAGTTTTACATTAAAATCAATAATGGAA
BEAU   TGGTTCTCAGCTTCTTGAGAACCAGTTTTACATCAAAATCAATAATGGAA 1710        1720        1730        1740        1750
6/82   CTCGTCGTTCTAGACGCTCTATTACTGGGAATGTTACAAATTGTCCTTAT
M41    CACGTCGTTTTAGACGTTCTATTACTGAAAATGTTGCAAATTGCCCTTAT
BEAU   CACGTCGTTTTAGACGTTCTATTACTGAAAATGTTGCAAATTGCCCTTAT 1760        1770        1780        1790        1800
6/82   GTTACTTATGGCAAGTTTTGTATAAAACCTGATGGTTCAATTTCCACACC
M41    GTTAGTTATGGTAAGTTTTGTATAAAACCTGATGGTTCAATTGCCACAAT
BEAU   GTTAGTTATGGTAAGTTTTGTATAAAACCTGATGGCTCAATTGCCACAAT 1810        1820        1830        1840        1850
6/82       ACCAAAAGAATTGGAACATTTTGTGGCACCTCTACTTAATGTAACTG
M41    AGTACCAAAACAATTGGAACAGTTTGTGGCACCTTTACTTAATGTTACTG
BEAU   AGTACCAAAACAATTGGAACAGTTTGTGGCACCTTTATTTAATGTTACTG 1860        1870        1880        1890        1900
6/82   AAAATGTGCTCATACCTGACAGTTTTAATTTAACAGTCACTGATGAGTAC
M41    AAAATGTGCTCATACCTAACAGTTTTAATTTAACTGTTACAGATGAGTAC
BEAU   AAAATGTGCTCATACCTAACAGTTTCAACTTAACTGTTACAGATGAGTAC 1910        1920        1930        1940        1950
6/82   ATACAAACGCGTATGGATAAGGTCCAAATTAATTGCCTTCAGTATGTTTG
M41    ATACAAACGCGTATGGATAAGGTCCAAATTAATTGTCTGCAGTATGTTTG
BEAU   ATACAAACGCGTATGGATAAGGTCCAAATTAATTGCCTGCAGTATGTTTG 1960        1970        1980        1990        2000
6/82   CGGCAATTCTTTGGAGTGTAGAAAGTTGTTTCAA
M41    TGGCAATTCTCTGGATTGTAGAGATTTGTTTCAACAATATGGGCCTGTTT
BEAU   TGGCAGTTCTCTGGATTGTAGAAAGTTGTTTCAACAATATGGGCCTGTTT 2010        2020        2030        2040        2050
M41    GTGACAACATATTGTCTGTAGTAAATAGTATTGGTCAAAAAGAAGATATG
BEAU   GCGACAACATATTGTCTGTAGTAAATAGTGTTGGTCAAAAAGAAGATATG 2060        2070        2080        2090        2100
M41    GAACTTTTGAATTTCTATTCTTCTACTAAACCGGCTGGTTTTAATACACC
BEAU   GAACTTTTGAATTTCTATTCTTCTACTAAACCGGCTGGTTTTAATACACC 2110        2120        2130        2140        2150
M41    ATTTCTTAGTAATGTTAGCACTGGTGAGTTTAATATTTCTCTTCTGTTAA
BEAU   AGTTCTTAGTAATGTTAGCACTGGTGAGTTTAATATTTCTCTTCTGTTAA 2160        2170        2180        2190        2200
6/82                                                              C
M41    CAACTCCTAGTAGTCCTAGAAGGCGTTCTTTTATTGAAGACCTTCTATTT
BEAU   CAAATCCTAGTAGTCGTAGAAAGCGTTCTCTTATTGAAGACCTTCTATTT 2210        2220        2230        2240        2250
6/82   ACAAGTGTTGAATCTGTTGGATTACCAACAGATGACGCATACAAGAAGTG
M41    ACAAGCGTTGAATCTGTTGGATTACCAACAGATGACGCATACAAAAATTG
BEAU   ACAAGCGTTGAATCTGTTGGACTACCAACAAATGACGCATATAAAAATTG 2260        2270        2280        2290        2300
6/82   CACTGCAGGACCTTTAGGCTTTCTTAAGGACCTAGCGTGTGCTCGTGAAT
M41    CACTGCAGGACCTTTAGGTTTTCTTAAGGACCTTGCGTGTGCTCGTGAAT
BEAU   CACTGCAGGACCTTTAGGCTTTTTTAAGGACCTTGCGTGTGCTCGTGAAT 2310        2320        2330        2340        2350
6/82   ATAATGGTTTGCTTGTGTTGCCTCCTATTATAACAGCAGAAATGCAAACC
M41    ATAATGGTTTGCTTGTGTTGCCTCCCATTATAACAGCAGAAATGCAAACT
BEAU   ATAATGGTTTGCTTGTGTTGCCTCCTATCATAACAGCAGAAATGCAAGCT
```

-continued

```
            2360           2370           2380           2390           2400
6/82   TTGTATACTAGTTCTCTAGTAGCTTCTATGGCTTTTGGTGGTATTACTTC
M41    TTGTATACTAGTTCTCTAGTAGCTTCTATGGCTTTTGGTGGTATTACTGC
BEAU   TTGTATACTAGTTCTCTAGTAGCTTCTATGGCTTTTGGTGGTATTACTGC 2410           2420           2430           2440           2450
6/82   AGCTGGTGCTATACCTTTCGCCACACAACTGCAGGCTAGAATTAATCATT
M41    AGCTGGTGCTATACCTTTTGCCACACAACTGCAGGCTAGAATTAATCACT
BEAU   AGCTGGTGCTATACCTTTTGCCACACAACTGCAGGCTAGAATTAATCACT 2460           2470           2480           2490           2500
6/82   TGGGTATCACCCAGTCACTCTTGTTTAAGAATCAAGAAAAAA
M41    TGGGTATTACCCAGTCACTTTTGTTGAAGAATCAAGAAAAAATTGCTGCT
BEAU   TGGGTATTACCCAGTCACTTTTGTTGAAGAATCAAGAAAAAATTGCTGCT 2510           2520           2530           2540           2550
M41    TCCTTTAATAAGGCCATTGGTCGTATGCAGGAAGGTTTTAGAAGTACATC
BEAU   TCCTTTAATAAGGCCATTGGTCATATGCAGGAAGGTTTTAGAAGTACATC 2560           2570           2580           2590           2600
M41    TCTAGCATTACAACAAATTCAAGATGTTGTTAATAAGCAGAGTGCTATTC
BEAU   TCTAGCATTACAACAAATTCAAGATGTTGTTAGTAAACAGAGTGCTATTC 2610           2620           2630           2640           2650
M41    TTACTGAGACTATGGCATCACTTAATAAAAATTTTGGTGCTATTTCTTCT
BEAU   TTACTGAGACTATGGCATCACTTAATAAAAATTTTGGTGCTATTTCTTCT 2660           2670           2680           2690           2700
M41    GTGATTCAAGAAATCTACCAGCAACTTGACGCCATACAAGCAAATGCTCA
BEAU   GTGATTCAAGAAATCTACCAGCAATTTGACGCCATACAAGCAAATGCTCA 2710           2720           2730           2740           2750
M41    AGTGGATCGTCTTATAACTGGTAGATTGTCATCACTTTCTGTTTTAGCAT
BEAU   AGTGGATCGTCTTATAACTGGTAGATTGTCATCACTTTCTGTTTTAGCAT 2760           2770           2780           2790           2800
M41    CTGCTAAGCAGGCGGAGCATATTAGAGTGTCACAACAGCGTGAGTTAGCT
BEAU   CTGCTAAGCAGGCGGAGTATATTAGAGTGTCACAACAGCGTGAGTTAGCT 2810           2820           2830           2840           2850
6/82            AAATTAATGAGTGTGTTAAATCTCAATCTATTAGGTATTCATT
M41    ACTCAGAAAATTAATGAGTGTGTTAAGTCACAGTCTATTAGGTACTCCTT
BEAU   ACTCAGAAAATTAATGAGTGTGTTAAGTCACAGTCTATTAGGTACTCCTT 2860           2870           2880           2890           2900
6/82   TTGTGGTAATGGAAGACATGTTCTAACCATACCACAAAATGCTCCTAATG
M41    TTGTGGTAATGGACGACATGTTCTAACCATACCGCAAAATGCACCTAATG
BEAU   TTGTGGTAATGGACGACATGTTCTAACCATACCGCAAAATGCACCTAATG 2910           2920           2930           2940           2950
6/82   GCATAGTGTTTATACACTTTACATACACGCCAGAGAGTTTTGTCAATGTG
M41    GTATAGTGTTTATACACTTTTCTTATACTCCAGATAGTTTTGTTAATGTT
BEAU   GTATAGTGTTTATACACTTTTCTTATACTCCAGATAGTTTTGTTAATGTT 2960           2970           2980           2990           3000
6/82   ACGGCAATAGTAGGGTTTTGTGTAAACCCAGCTAATGCTAGCCAGTATGC
M41    ACTGCAATAGTGGGTTTTTGTGTAAAGCCAGCTAATGCTAGTCAGTATGC
BEAU   ACTGCAATAGTGGGTTTTTGTGTAAAGCCAGCTAATGCTAGTCAGTATGC 3010           3020           3030           3040           3050
6/82   AATAGTGCCTGCTAATGGCAGAGGTATTTTTATACAAGTTAATGGTAGTT
M41    AATAGTACCCGCTAATGGTAGGGGTATTTTTATACAAGTTAATGGTAGTT
BEAU   AATAGTGCCCGCTAATGGTAGGGGTATTTTTATACAAGTTAATGGTAGTT 3060           3070           3080           2090           3100
6/82   ACTACATCACTGCAAGAGATATGTATATGCCAAGAGATATTACTGCAGGA
M41    ACTACATCACAGCACGAGATATGTATATGCCAAGAGCTATTACTGCAGGA
BEAU   ACTACATCACTGCACGAGATATGTATATGCCAAGAGCTATTACTGCAGGA 3110           3120           3130           3140           3150
6/82   GATATAGTTACGCTTACTTCGTGTCAAGCAAATTATGTAAGTGTAAATAA
M41    GATATAGTTACGCTTACTTCTTGTCAAGCAAATTATGTAAGTGTAAATAA
BEAU   GATGTAGTTACGCTTACTTCTTGTCAAGCAAATTATGTAAGTGTAAATAA 3160           3170           3180           3190           3200
6/82   GACCGTCATTACTACATTTGTAGACAATGATGATTTTGATTTTGATGACG
M41    GACCGTCATTACTACATTCGTAGACAATGATGATTTTGATTTTAATGACG
BEAU   GACCGTCATTACTACATTCGTAGACAATGATGATTTTGATTTTAATGACG 3210           3220           3230           3240           3250
6/82   AGTTGTCAAAATGGTGGAATGATACTAAGCATGAGCTACCAGACTTTGAC
M41    AATTGTCAAAATGGTGGAATGACACTAAGCATGAGCTACCAGACTTTGAC
```

-continued
```
BEAU  AATTGTCAAAATGGTGGAATGATACTAAGCATGAGCTACCAGACTTTGAC 3260       3270       3280       3290       3300
6/82   GAATTCAATTATACAGTACCTATACTTGATATTGGTAGTGAAATTGATCG
M41    AAATTCAATTACACAGTACCTATACTTGACATTGATAGTGAAATTGATCG
BEAU   AAATTCAATTACACAGTACCTATACTTGACATTGATAGTGAAATTGATCG 3310       3320       3330       3340       3350
6/82   TATTCAAGGTGTTATACAGGGCCTTAATGACTCTCTAATAGACCTTGAAA
M41    TATTCAAGGCGTTATACAGGGTCTTAATGACTCTTTAATAGACCTTGAAA
BEAU   TATTCAAGGCGTTATACAGGGTCTTAATGACTCTCTAATAGACCTTGAAA 3360       3370       3380       3390       3400
6/82   CCCTTTCAATACTTAAGACTTATATTAAATGGCCTTGGTATGTGTGGCTT
M41    AACTTTCAATACTCAAAACTTATATTAAGTGGCCTTGGTATGTGTGGTTA
BEAU   AACTTTCAATACTCAAAACTTATATTAAGTGGCCTTGGTATGTGTGGTTA 3410       3420       3430       3440       3450
6/82   GCCATTGCATTCCTTACCATTATCTTTATTCTGGT
M41    GCCATAGCTTTTGCCACTATTATCTTCATCTTAATACTAGGATGGGTTTT
BEAU   GCCATAGCTTTTGCCACTATTATCTTCATCTTAATACTAGGATGGGTTTT 3460       3470       3480       3490       3500
M41    CTTCATGACTGGATGTTGTGGTTGTTGTTGTGGATGCTTTGGCATTATGC
BEAU   CTTCATGACTGGTTGTTGTGGTTGTTGTTGTGGATGCTTTGGCATTATGC 3510       3520       3530       3540       3550
M41    CTCTAATGAGTAAGTGTGGTAAGAAATCTTCTTATTACACGACTTTTGAT
BEAU   CTCTAATGAGTAAGTGTGGTAAGAAATCTTCTTATTACACGACTTTTGAT 3560       3570       3580       3590       3600
M41    AACGATGTGGTAACTTAACAATACAGACCTAAAAAGTCTGTTTAATGATT
BEAU   AACGATGTGGTAACTGAACAATACAGACCTAAAAAGTCTGTTTGATGATC 3610       3620       3630       3640       3650
M41    CAAAGTCCCACGTCCTTCCTAATAGTATTAATTCTTCTTTGGTGTAAACT
BEAU   CAAAGTCCCACGTCCTTCCTAATAGTATTAATTCTTCTTTGGTGTAAACT 3660       3670       3680       3690       3700
M41    T
BEAU   T
```

The IBV RNA of many other strains is believed to be fairly similar to that of Beaudette, M41 or 6/82 and therefore DNA molecules of the present invention can be used as probes for hybridisation to RNA of other serotypes, thus enabling spike cDNA of other strains to be identified and prepared. For example, cDNA from other IBV strains of the Massachusetts serotype or the live vaccine strains H52 and H120 used in the UK, believed to be similar to M41 could be prepared from M41 or Beaudette cDNA. Any of the Dutch type strains in the serogroups known as D207, D212, D3128, and D3896, believed to be similar to strain 6/82 (Houghton Poultry Research Station, Huntingdon, England), could be prepared using 6/82 DNA and probably from M41 or Beaudette cDNA. Even if the overall degree of homology between any of these IBVs and the starting strain IBV (i.e. Beaudette, M41 or 6/82) is not high enough to allow hybridisation over a substantial length of sequence, it can confidently be expected that there will be some lengths of at least 13 nucleotides, and more desirably at least 18 nucleotides, which have very high homology, allowing series of such probes to be constructed from starting strain IBV spike cDNA. Some of these probes will hybridise to cDNA of the RNA of the other IBV. By probing a library of such cDNA, spike protein cDNA of the other IBV can be identified and obtained. Alternatively, the "random priming" method described above for preparation of M41 and 6/82 cDNA from Beaudette can be used to prepare cDNA from any strain.

The invention therefore also includes particularly DNA molecules coding for IBV spike protein polypeptide having a reasonable degree of homology of nucleotide sequence with IBV Beaudette, M41 or 6/82 strain to allow hybridisation to take place. The suggested minimum degree of nucleotide sequence homology is 75%, but at least 80% is preferred and a degree of homology of 85-100% would be useful in normally allowing hybridisation to take place under reasonably stringent conditions. (Obviously, if the DNA is to be used in typing viruses one would perform a probe hybridisation under far more stringent conditions).

It will be appreciated that the degree of freedom in the genetic code in that most amino acids are coded for by any of 2, 4 or 6 codons will allow point substitution of nucleotides without altering the polypeptide coded for. Thus it is appropriate also to consider amino acid sequence homology, in relation to a possible use of the DNA for expression to prepare artificial polypeptides and in anticipation that such substitutions will account for many of the differences of nucleotide sequence between different IBV types or strains. A degree of homology of amino acid sequence of 80-100%, especially 90-100%, most especially 95-100% is specifically contemplated herein for cDNA prepared from other IBV types or strains compared with the starting strain.

The invention further includes a DNA molecule defined in a slightly different way as comprising (consisting of or including) a strand which is complementary to at least the body of IBV Beaudette, M41 or 6/82 strain mRNA E or a portion thereof comprising (consisting of or including) S1 polypeptide or antigenic determinants thereof, or to a said mRNA E or portion thereof having at least 75%, preferably at least 80%, nucleotide sequence homology therewith. Particularly included is such a cDNA for that part of said mRNA E which does not overlap with the body of mRNA D but extends 5'-wards therebeyond (see the drawing).

Plasmids, in bacterial hosts, have been deposited as Budapest Treaty patent deposits as detailed hereinafter. Conveniently the homologies referred to immediately and further above are with reference to the spike protein precursor-coding cDNA incorporated in these plasmids, or, indeed, with the whole plasmid DNA.

The S1 and S2 DNA of the invention need not contain the full length of DNA coding for these polypeptides. Particularly, epitope (antigenic determinant)-coding regions can be located by sequencing the corresponding part of other IBV strains and comparing them. The major antigenic determinants are likely to be those showing the greatest heterology. Such a region has been identified as encoded by nucleotides 449–459, approximately, in sequence formula (2). Also, these regions are likely to lie accessibly in the conformational structure of the proteins. One or more such antigenic determinants can be prepared by chemical synthesis or recombinant DNA technology, as is most convenient, and if desired linked together or linked to other sequences of IBV spike protein DNA.

The S1 or S2 DNA might conveniently be truncated or cut off short of either terminus, especially at the 3' end of S1 or 5' end of S2, since it is usually possible to dispense with a short sequence at the terminus. It might even be convenient to do so, in order to excise the S1 DNA in a convenient place for which there is a 'unique' restriction endonuclease site. Thus the DNA could be truncated by, say, 1–30, more safely 1–15, nucleotides at either end.

The extent and nature of any flanking sequences at either end of the DNA of the invention is in essence irrelevant and will normally depend on the particular use to which the spike protein polypeptide DNA is to be put. It might be desirable, for example, to ligate the S1 DNA to foreign gene sequences, or to homopolynucleotide tail sequences, whereby a foreign gene could be more easily attached. Flanking sequences from IBV cDNA itself could be present, whether they are those which are complementary to flanking DNA in the genomic or mRNA E of the IBV or not. Such flanking IBV cDNA sequences will not usually exceed 100 nucleotides at either end of the cDNA and could be quite short, e.g. up to 20 nucleotides. It must be understood, however, that when the cDNA of the invention is inserted in a vector, for example a plasmid, cosmid, phage or viral vector, the foreign DNA sequences inherently present or introduced into the vector and joined to the cDNA of the invention will be of very substantial length, and thus the above statements of preference do not apply to foreign DNA.

The vectors included in the invention are cloning and expression vectors. The IBV spike DNA is conveniently multiplied by insertion in a vector, for example pBR322, and cloning in an appropriate host such as a bacterial host, especially E. coli or Bacillus species, or a yeast. For expression, mammalian cells can be transfected by the calcium phosphate precipitation method or transformed by a viral vector. Viral vectors include retroviruses and poxviruses such as fowlpox virus or vaccinia virus.

The IBV DNA can be introduced into the viral vector as follows. The spike DNA is inserted into a plasmid containing an appropriate poxvirus gene, such as the thymidine kinase gene of vaccinia virus, so that the insert interrupts the gene sequence. A virus promotor is also introduced into the gene sequence in such a position that it will operate on the inserted spike DNA sequence. When the poxvirus and the plasmid recombinant DNA are co-transfected into a mammalian cell, homologous recombination takes place between the poxvirus gene, such as TK in vaccinia virus, and the same gene present in the plasmid. Since the IBV spike DNA has thereby interrupted the poxvirus gene, viruses lacking the gene expression product, such as TK, are selected. Once such a recombinant virus vector has been thus constructed it can be used to introduce the IBV spike DNA directly into the desired host cells without the need for any separate step of transfecting plasmid recombinant DNA into the cells.

With a view ultimately to obtaining expression of the recombinant virus in vivo, the preferred poxvirus is fowlpox virus. It may be that the inserted IBV DNA contains a sequence, which, in the fowlpox vector, lead to premature termination of transcription. In this case, the spike DNA would have to be modified slightly by one or two nucleotides, thereby to allow transcription to proceed along the full length of the gene.

The vector can be introduced into any appropriate host in any method known in recombinant DNA technology. Hosts include E. coli, Bacillus spp, mammalian cells, and yeasts. The method of introduction can be transformation by a plasmid or cosmid vector, or infection by a phage or viral vector etc. as known in recombinant DNA technology.

For use as diagnostic probes the DNA of the invention which includes coding strand and/or its complement can be labelled in any conventional way, e.g. by radiolabelling, preferably with $^{32}$P, enzyme labelling by the method of D. C. Ward et al., European Patent Specification No. 63879 or A. D. B. Malcolm et al., PCT Patent Specification WO84/03250 or fluorescently, see CNRS European Patent Specification No. 117,177.

The following Examples illustrate the invention. All temperatures are in °C.

EXAMPLE 1

1. Selection and synthesis of an oligonucleotide primer

A cDNA extending from approximately nucleotides 1000 to 3300 of the IBV Beaudette strain genomic RNA has been cloned in E. coli HB 101 and designated clone C5.136, see T. D. K. Brown and M. E. G. Boursnell, Virus Research 1, 15–24 (1984) and M. E. G. Boursnell, T. D. K. Brown and M. M. Binns, ib. id. 1, 303–313 (1984). The genomic map of the accompanying drawing shows C5.136 and the approximate position of a 13-base 'primer' sequence near its 5' end. This 13-base sequence is that selected for priming the synthesis of the cDNA from the spike protein coding region of IBV genomic RNA.

The 13-base primer sequence is located at nucleotides 256 to 268 read in the viral transcript 5'→3' direction. In the following partial sequence of the transcript, designated sequence formula (3), these nucleotides are underlined:

```
        10          20          30         (3)
   AAGAACGGTT GGAATAATAA AAATCCAGCA 40          50          60
   AATTTTCAAG ATGCCCAACG AGACAAATTG 70          80          90
   TACTCTTGAC TTTGAACAGT CAGTTCAGCT
```

-continued

```
           100        110        120
    TTTTAAAGAG TATAATTTAT TTATAACTGC 130        140        150
    ATTCTTGTTG TTCTTAACCA TAATACTTCA 160        170        180
    GTATGGCTAT GCAACAAGAA GTAAGGTTAT 190        200        210
    TTATACACTG AAAATGATAG TGTTATGGTG 220        230        240
    CTTTTGGCCC CTTAACATTG CAGTAGGTGT 250        260        270
    AATTTCATGT ACATACCCAC CAAACACAGG 280        290        300
    AGGTCTTGTC GCAGCGATAA TACTTACAGT 310        320        330
    GTTTGCGTGT CTGTCTTTTG TAGGTTATTG 340        350        360
    TATCCAGAGT ATTAGACTCT TTAAGCGGTG
```

The sequence of the primer was chosen on the basis of its position in the C5.136 sequence (close to the 5' terminus of the clone) and its lack of self-complementarity. Although an oligonucleotide sequence of only 13 nucleotides would not necessarily be unique, extensive sequencing of the entire length of C5.136 carried out in connection with the present invention has shown that it is unique within C5.136.

The primer used was the reverse complement of the above-shown 13-base sequence, i.e. was of formula (4)

$$5' \text{ TGTGTTTGGTGGG } 3' \qquad (4)$$

It was synthesised using the phosphotriester method as described by M. J. Gait et al., Nucleic Acids Research 10, 6243–6254 (1982).

2. Primed synthesis of ds-cDNA from viral RNA

Genomic RNA of the Beaudette strain of IBV was isolated from purified virions as described by T. D. K. Brown and M. E. G. Boursnell supra, at page 16. cDNA was synthesised from the genomic RNA using the method of U. Gubler and B. J. Hoffman, Gene 25, 263–269 (1983).

cDNA was synthesised as follows: the first strand reaction was carried out in 50 microliters of deionised water containing 0.05M Tris-HCl pH 8.7 at 25°, 0.01M MgCl$_2$, 0.01M dithiothreitol, 0.004M sodium pyrophosphate, 0.001M each of dATP, dCTP, dGTP and dTTP, 40 units of human placental RNase inhibitor, 0.8 microgram of the synthetic oligonucleotide primer described above, 10 microcuries of (alpha-$^{32}$P)-labelled dCTP, approximately 20 micrograms of the IBV genomic RNA and 160 units of AMV reverse transcriptase. The reaction mixture was incubated at 43° for 1 hour. The first strand cDNA was extracted twice with phenol/chloroform methyl butanols (50:49:1 v/v/v), including 1 g/liter 8-hydroxyquinoline, equilibrated with 10 mM Tris-HCl pH 7.5, 1 mM EDTA and subjected to two ethanol precipitations in the presence of ammonium acetate.

The second strand synthesis reaction mixture contained in 100 microliters of deionised water 0.02M Tris-HCl pH 7.5, 0.005M MgCl$_2$, 0.01M (NH$_4$)$_2$SO$_4$, 0.1M KCl, 0.15 mM beta-NAD, 0.04 mM dATP, dCTP, dGTP and dTTP, 50 micrograms bovine serum albumin, 10 microcuries of (alpha-$^{32}$P)-labelled dCTP, 22.5 units of E. coli DNA polymerase 1, 10 units of RNase H, and 1 unit of E. coli DNA ligase (NAD-dependent). The reaction mixture was incubated for 1 hour at 12° and then for 1 hour at 22°. The reaction mixture was then phenol/chloroform extracted and ethanol-precipitated as described above.

3. Cloning of the cDNA dC homopolymer tails were added to the cDNA as follows: the cDNA was dissolved in 10 microliters of 10 mM Tris-HCl pH 7.5, 1 mM EDTA and added to a final reaction volume of 50 microliters containing 1x terminal transferase buffer (obtained from Bethesda Research Laboratories), 0.6 mM dCTP, 100 microcuries of ($^3$H)-dCTP, 100 micrograms bovine serum albumin and 50 units of terminal transferase. The reaction mixture was incubated at 37° for one hour, heated to 65° for 10 minutes and passed over a Sepharose CL-4B column. Fractions from the leading edge of the excluded peak were pooled and ethanol-precipitated. Approximately 1 microgram of double-stranded cDNA was obtained using this protocol. 250 ng of this cDNA was mixed with 2.5 micrograms of dG-tailed pBR322 plasmid (obtained from Bethesda Research Laboratories) and the mixture was ethanol-precipitated. The precipitate was dissolved in 40 microliters of 0.2M NaCl, 10 mM Tris-HCl pH 7.5, 1 mM EDTA and subjected to the following annealing regime. It was first heated to 65° for 5 minutes, rapidly cooled to 50° and then left to cool gradually to 42° in a waterbath. The annealing was then allowed to proceed overnight to 20°.

The annealed DNA was then transformed into E. coli strain LE392 (see, for example, Molecular Cloning—a Laboratory Manual, T. Maniatis, E. F. Fritsch and J. Sambrook, Cold Spring Harbor Laboratory, New York, 1982) using the method of D. Hanahan, Journal of Molecular Biology 166, 557–580 (1983).

4. Isolation of a plasmid from the cloned cDNA

The E. coli LE392 transformed as described above were grown and subjected to selection for tetracycline resistance. The tetracycline-resistant colonies were screened for IBV sequences by colony hybridisation to IBV genomic RNA. Thus, the cDNA was denatured and incubated with $^{32}$P end-labelled alkali-treated IBV genomic RNA as the hybridisation probe. The plasmid giving the strongest signal in the colony hybridisation was designated pMB179.

E. coli LE392 containing plasmid pMB179 has been deposited as a patent deposit under the Budapest Treaty on the International Recognition of the Deposit of Microorganisms for the Purposes of Patent Procedure on 13th June 1985 at the National Collection of Industrial Bacteria, Torry Research Station, P.O. Box 31, 135 Abbey Road, Aberdeen, Scotland AB9 8DG under the number NCIB 12102.

5. Sequencing of the RNA-positive cloned cDNA

Random subclones of pMB179 were generated by cloning either DNase1-treated or sonicated fragments into SmaI-cut, phosphatased M13 mp10 (Amersham International). Clones containing viral inserts were identified by colony hybridisation with $^{32}$P end-labelled alkali-treated IBV RNA or $^{32}$P end-labelled reverse-transcribed viral probes. In addition PstI and RsaI fragments were cloned into PstI-digested M13 mp11 and SmaI-cut, phosphatased M13 mp10 respectively.

M13 dideoxy sequencing was carried out using (alpha-$^{35}$S)dATP (Amersham International), the complete sequence being obtained on both strands. Reverse sequencing was used to obtain the last sequences required. The products of the sequencing reactions were analysed on buffer gradient gels, see M. D. Biggin et al., Proc. Natl. Acad. Sci. USA 80, 3963–3965 (1983). A sonic digitiser (Graf/Bar, Science Accessories Corporation) was used to read data into a BBC microcomputer, and data was analysed on a VAX 11/750, using the programs of R. Staden, Nucleic Acids Research 10, 4731–4751 (1982) and ib. id. 12, 521–538 (1984).

6. Isolation of IBV S1 and S2 polypeptides

IBV, strain Beaudette, was obtained from Dr Bela Lomniczi, Budapest. All subsequent virus growth was in monolayers of primary chick kidney (CK) cells, prepared by the method of Youngner (1954). The virus was passaged six times in CK cells and was then plaque-purified three times. The virus in one of these plaques was passaged once to produce a working stock of virus.

For radiolabelling two 9 cm plastic dishes of CK cells were washed twice with Eagle's minimal essential medium (EMEM) and inoculated with 4 ml of working stock plus 4 ml of fresh EMEM containing 0.2% bovine serum albumin (BSA). After 90 minutes at 37° in a 5%/95% $CO_2$/air atmosphere the inoculum was removed and replaced by 8 ml of EMEM. After 4.5 hours at 37° the medium was removed and replaced with 8 ml of EMEM containing 500 microcuries of $^3$H-serine and 0.2% BSA. After a further 18 hours at 37° the medium was recovered, clarified, calf serum (to provide a source of protein) was added (2%) and an equal volume of saturated ammonium sulphate added. After the mixture, surrounded by melting ice, had been stirred for 3 hours the precipitate was recovered by low speed centrifugation, dissolved in 1 ml of NET buffer (100 mM sodium chloride, 1 mM of NaEDTA, 10 mM Tris-HCl, pH 7.4) and placed on a 25–55% (w/w) sucrose gradient in NET containing 100 micrograms/ml of BSA. After centrifugation at 30,000 g average for 16 hours at 4° the gradient was fractionated. Fractions containing virus were pooled, diluted 2.5-fold and the virus pelleted by centrifugation at 90,000 g maximum for 3 hours at 4°. The pellets were dissolved in 62.5 mM Tris-HCl pH 7.0 containing 2% SDS and 2% 2-mercaptoethanol at 100° for 2 minutes. The viral polypeptides were separated by SDS-polyacrylamide gel electrophoresis, in a gel containing a 5–10% acrylamide gradient, using the buffers of U. K. Laemmli, Nature 227, 680–685 (1970). After electrophoresis the gel was soaked in 30 volumes of 1M sodium salicylate in water for 30 minutes. The gel was dried under vacuum and the polypeptides located by exposure of X-ray film to the gel. The S1 polypeptide is that of highest molecular weight. The developed, dried X-ray film was placed over the dried gel and the region of the gel containing the S1 and S2 polypeptides was cut out. The polypeptides were eluted from the gel by the procedure described by W. J. Welch et al., Journal of Virology 38, 968–972 (1981), extensively dialysed against distilled water containing 0.03% SDS and lyophilised. The powdered protein was dissolved in 200 microliters of 0.1M sodium bicarbonate containing 4% SDS and added to 100 mg of p-phenylenediisothiocyanate-treated glass (17 nm pore size) prepared by the method of E. Wachter et al., FEBS Letters 35, 97–102 (1973). Following incubation for 90 minutes at 56° under nitrogen the glass was washed with water and methanol to remove non-covalently bound material.

7. Amino acid sequencing

The glass-coupled polypeptide was then partially sequenced at the amino end by automated solid-phase Edman degradation, M. Brett and J. B. C. Findlay, Biochemical Journal 211, 661–670 (1983). The results indicated the presence in the S1 polypeptide of serine residues at positions 5, 6, 7, 14, and 20 (counting from the N-terminal end). These results unambiguously confirmed the sequence of the S1 DNA within the open reading frame. The amino acid data indicated that an 18 amino acid signal sequence MLVTPLLLVTLLCALCSA having a typical hydrophobic core and small neutral residues, alanine (A) and cysteine (C), at positions -1 and -3 from the cleavage site is cleaved from S1 during post-translational processing. The signal sequence is shown boxed in the IBV spike protein cDNA sequence formula (1) above and the region coding for the S1 N-terminus (VLYDSSSYV . . . ) begins at nucleotide 155 in the sequence shown.

Amino acid sequencing of the S2 polypeptide indicated a serine residue at amino acid position 13 from the N-terminal end.

Two other interesting structural features of the spike precursor protein were revealed by analysis of the amino acid sequence predicted from the nucleotide sequence. Firstly, the sequence contains twenty-eight potential sites for N-glycosylation (assuming that Asn-Pro-Thr and Asn-Pro-Ser are not used) which are shown by filled circles in the sequence formula (1) above. Secondly, a hydrophilicity plot of the amino acid sequence, in the manner of J. Kyte et al., Journal of Molecular Biology 157, 105–132 (1982), showed a hydrophobic region which contains 44 non-polar amino acids preceding the charged amino acids at the carboxy-terminus of the S2 polypeptide. This hydrophobic structure probably anchors the spike protein to the viral envelope as has been proposed for similar structures on human influenza virus and fowl plague virus haemagglutinins. This region is coded for by nucleotides 3374 to 3505 and is indicated by dotted underlining in the sequence formula (1) above.

The underlined sequences at nucleotides 39 to 50 and 3556 to 3567 showing high mutual homology are the regions corresponding to the 5′ ends of the bodies of mRNA E and D respectively.

EXAMPLE 2

In a procedure analogous to that of Example 1 a cDNA coding for the spike protein precursor of IBV strain M41 was prepared. The method of Example 1 was repeated using in stage (1) a 15-base primer oligonucleotide of sequence complementary to part of the sequence of the IBV Beaudette cDNA of plasmid pMB179. The primer was the reverse complement of the 15 bases numbered 3605 to 3619 in formula (1) above, i.e. was of formula (5):

5′ CTATTAGGAAGGACG 3′          (5)

Stage (4) gave rise to a plasmid pMB233 in *E. coli* LE392, which has also been deposited as a patent deposit under the Budapest Treaty on 13th June 1985 at the National Collection of Industrial Bacteria, under the number NCIB 12101. The IBV cDNA in this plasmid was found to extend 5′-wards from the primer for approximately 2200 base pairs.

In stage (5) sub-clones were generated from PstI-cut fragments of pMB233 in PstI-digested M13 mp10, and M13 dideoxy sequencing was carried out on sub-clones coding for the S1/S2 protein junction. Formula (5) below shows a partial sequence, in the region of the S1/S2 protein junction:

(6)

```
                           ↓
  •  N   G   T   R   R   F   R   R   S   I   T   E
    AATGGAACACGTCGTTTTAGACGTTCTATTACTGAAA
    1690       1700      1710      1720

N   V   A   N   C   P   Y   V   S   Y   G   K   F
    ATGTTGCAAATTGCCCTTATGTTAGTTATGGTAAGTTT
       1730      1740      1750      1760

C   I   K
    TGTATAAAA
      1770
``` which is identical with the IBV Beaudette strain cDNA sequence of formula (1). The same nomenclature is used in formula (6), the arrow denoting the 5'-end of the S2-coding region.

Figure 2:
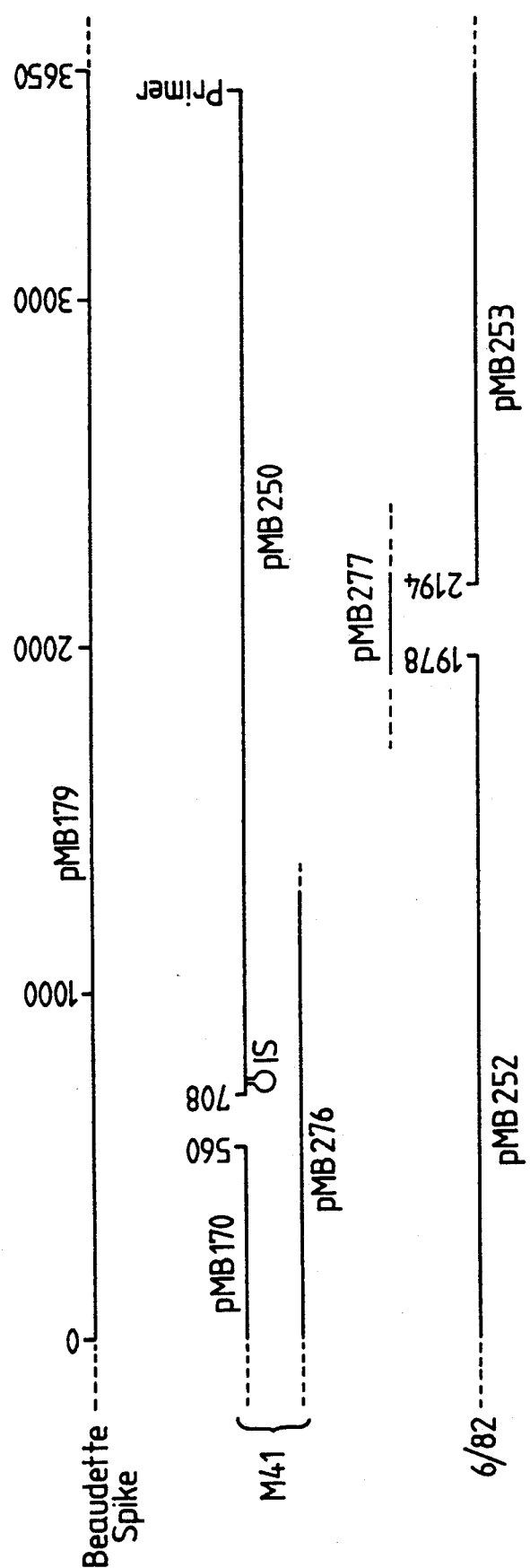
FIG. 2 is a map of recombinant DNA which defines certain plasmids containing IBV spike cDNA of strains M41 and 6/82.

The entire M41 spike sequence has been inserted in two plasmids pMB 276 and pMB 250, and cloned in *E. coli* by a similar method to that described for pMB 233 above. Sub-clones were then made in M13 mp10 as described for pMB 233. Using these clones and another clone, pMB 170, similarly prepared, the entire spike sequence of M41 was obtained. The positions of pMB 276, pMB 250 and pMB 170 relative to the Beaudette plasmid pMB 179 are shown in FIG. 2 of the drawings. Plasmid pMB 250 contained a small insertion sequence of other foreign DNA shown as "IS" in FIG. 2. This can readily be removed when it is desired to make a full length copy of the M41 spike sequence.

In stage (6) the S1 and S2 polypeptides of the M41 strain of IBV were isolated similarly. The virus was grown in de-embryonated chicken eggs as described by D. Cavanagh, Journal of General Virology 53, 93–101 (1981) and radiolabelled with 1 milliCurie of $^3$H leucine, $^3$H isoleucine or $^3$H valine plus 100 microcuries of $^{35}$S methionine. After electrophoresis of the viral proteins in polyacrylamide gels, the gels were immediately dried under vacuum and the polypeptides located by exposure of X-ray film to the gel.

Partial amino acid sequence analysis of the amino-terminal of radiolabelled S2 from IBV M41 confirmed this sequence, by showing that there are isoleucine residues at positions 2 and 19 from the N-terminal, valine residues at 6 and 12, and no leucine residue in the first 20 amino acids.

Partial amino acid sequence analysis of S1 from IBV M41 showed a leucine residue at position 2 from the N-terminal end and a valine residue at position 9. These results are in agreement with the IBV Beaudette cDNA sequence.

Although the spike protein precursor coding cDNA of M41 appears to be highly homologous with that of Beaudette strain, there is a distinction between the two at the 3'-end. In M41 one of the nucleotides of the homology region corresponding to Beaudette 3556 to 3567 has changed. Number 3560 is a thymine base (T) instead of a guanine base (G), indicating that a stop codon UAA is present in the M41 RNA. It follows that the 3'-end of the Beaudette cDNA ends with the nucleotide sequence ... GTGGTAACT and the last 9 amino acids, at the carboxyl-terminus end of the Beaudette spike protein presursor, are not coded for in M41 strain cDNA.

EXAMPLE 3

This Example describes the cloning and sequencing of IBV spike cDNA of strain 6/82.

Oligodeoxynucleotides were prepared from calf thymus DNA (Sigma) by treatment with pancreatic DNase and size fractionation on DEAE-cellulose. IBV genomic RNA for strain 6/82 was prepared as described for Beaudette strain in Example 1. cDNA synthesis was carried out using the method of U. Gubler and B. J. Hoffman, supra. Thus, approximately 20 micrograms of virion RNA and 100 micrograms of calf thymus oligonucleotide primers in a reaction volume of 50 microliters (50 mM Tris-HCl pH 8.3, 10 mM MgCl$_2$, 10 mM DTT, 4 mM sodium pyrophosphate, 1.25 mM dNTPs were incubated with 160 units of AMV reverse transcriptase at 43° C. for 30 minutes. After stopping the reaction with 20 mM EDTA followed by phenol extraction, the products were precipitated with ethanol and ammonium acetate. For second-strand synthesis the products were resuspended in 100 microliters of 20 mM Tris-HCl, pH 7.5, 5 mM MgCl$_2$, 10 mM (NH$_4$)$_2$SO$_4$, 100 mM KCl, 0.15 mM beta-NAD, 50 micrograms ml BSA, and 40 micromolar dNTPs. 22.5 units of DNA Polymerase 1 (Biolabs), 2.5 units of RNaseH (BRL), and 5 units of *E. coli* DNA ligase (Biolabs) were added to the reaction which was incubated at 12° C. for 60 minutes and then at 22° C. for 60 minutes. The products were phenol-extracted twice and precipitated with ethanol and ammonium acetate. Double-stranded cDNA was tailed with dC residues, size-fractionated on CL Sepharose 4B, and cloned into dG-tailed PstI-cleaved pBR322. This vector was used to transform *E. coli* LE392 by the method of D. Hanahan, supra and selection made for tetracycline-resistant colonies. Between 2 and 4×10$^4$ tetracycline-resistant clones were obtained in each experiment of which approximately 5% were derived from uncut vector molecules. Clones were screened for the presence of viral inserts by colony hybridisation using $^{32}$P-labelled, alkali-treated IBV 6/82 genomic RNA as a probe.

The viral inserts present in a number of clones which were strongly positive in the colony hybridisation assay were tested for whether they contained IBV spike sequence, by probing with $^{32}$P-labelled M13 sub-clones of pMB 179. Clones, pMB 252, 253 and 277, were isolated, which together encode all the 6/82 spike protein precursor (see FIG. 2 of the drawings). Sub-clones in M13 mp10 using PstI and RsaI were made and sequenced to give the data shown in FIG. 2. There are far more nucleotide changes in 6/82 than in M41, when compared to the Beaudette sequence.

*E. coli* LE392 containing plasmid pMB 252 has been deposited as a patent deposit under the Budapest Treaty on the International Recognition of the Deposit of Micro-organisms for the Purposes of Patent Procedure on 11th Mar. 1986 at the National Collection of Industrial Bacteria, Torry Research Station, P.O. Box 31, 135 Abbey Road, Aberdeen, Scotland AB9 8DG under the number NCIB 12221.

EXAMPLE 4

This Example illustrates the use of vaccinia virus as a vector for expression of IBV spike protein polypeptide in a mammalian cell line.

1. Insertion of IBV spike sequence into a vaccinia-compatible plasmid vector

Plasmid pMB 179 containing the IBV Beaudette spike DNA was digested with the restriction enzymes XbaI and TthIII. The restricted fragments were end-repaired with $T_4$ DNA polymerase using a BRL end-repair kit, and separated on a 1% agarose gel. The fragment containing the spike sequence flanked by non-coding sequences (total size 3,672 bases) was purified from agarose by the method of Dretzen et al., Analytical Biochemistry 112, 295-298 (1981). This fragment was ligated into the unique SmaI site of pGS20, a plasmid vector designed for the insertion of foreign sequences into the vaccinia virus thymidine kinase (TK) gene, described by Mackett, Smith & Moss, J. Virology, 49, 857-864 (1984). pGS20 has been widely distributed.

The following is a brief explanation of plasmid pGS20. pGS20 was constructed to contain the TK gene of vaccinia virus interrupted by (1) a vaccinia virus promoter sequence, followed immediately by (2) a sequence containing several different unique restriction endonuclease sites, whereby a foreign gene can be inserted into one of these sites.

The vaccinia virus promoter provides a signal for transcription of the foreign gene. When the foreign gene is inserted in pGS20, the following is the order of the various DNA sequences (shown in linear form for brevity and not to scale):

```
              7.5 K
              vaccinia    foreign
  "J"  TK gene promoter   gene    TK gene   "J"
|------|____|---|----|---|----|---|____|------|
```

The HindIII J fragment of vaccinia virus, containing the TK gene, is interrupted by the promoter of a vaccinia virus early gene encoding a 7.5 kb polypeptide and by the foreign gene which, in the present instance, is inserted into an SmaI restriction site in pGS20. When cells are transfected with the pGS20 plasmid containing the foreign gene and with vaccinia virus, "homologous recombination" occurs between the sites (call them A, B) on either side of the TK gene of pGS20, whereby the sequence A to B of the plasmid replaces the sequence A to B of the viral genome. Since pGS20 carries the foreign gene and a promoter, the virus will proceed to copy the foreign gene, in this case IBV spike protein precursor cDNA. The foreign gene is then translated under the influence of its own translation initiation site. The recombinant virus-infected cells are selected for by their inability to express TK, the TK gene having been inactivated by the insertions in it.

Following transformation of pGS20 containing the IBV Beaudette spike DNA into *E. coli* strain LE392, recombinant plasmids were identified by colony hybridisation to $^{32}$P-labelled nick-translated, gel-purified IBV spike DNA fragment. DNA from six of these was cut with HindIII, which cuts the spike sequence asymmetrically. One recombinant, pSB1, was selected which has the spike sequence in the correct orientation for insertion into vaccinia virus. The precise nucleotide sequence surrounding the junction between the vaccinia promoter in pGS20 and the inserted IBV spike DNA fragment was determined by Maxam & Gilbert sequencing to ensure that no incorrect translational start sequences had been accidentally introduced.

2. Recombination into vaccinia virus

Transfection procedures and selection of recombinants were carried out as described by Mackett, Smith & Moss in "DNA Cloning: a practical approach" vol. II, ed. Glover, IRL Press Ltd., Oxford 1985, pp 191-212. Monolayers of near confluent African green monkey kidney cells, CV-1 from Flow Laboratories Inc. in 25 cm$^2$ bottles were infected with one plaque-forming unit (pfu) per cell of vaccinia virus strain WR. One hour later the cells were washed with phosphate buffered saline and then transfected with 500 microliters per bottle of calcium phosphate-precipitated pSB1. The precipitate consisted of 20 micrograms pSB1, 1 microgram vaccinia virus DNA, 1 ml HEPES buffered saline, pH 7.12, and 50 microliters of 2M $CaCl_2$ and was left on the cells for 30 minutes. Cells were harvested 2 days later and progeny viruses plaque-purified in the presence of bromodeoxy uridine (BUdR) on TK$^-$143 cells available from the Wistar Institute Inc. (Other TK$^-$cells susceptible to vaccinia could be substituted). The TK$^-$selected viruses were grown up in small monolayers of TK$^-$cells and screened for the presence of spike sequences by dot-blotting onto nitrocellulose and probing with $^{32}$P-labelled nick-translated pMB179. Two positive recombinants, vaccinia-SP1 and vaccinia-SP2 were plaque-purified again on TK$^-$monolayers with BUdR selection, re-screened by dot-blotting then large stocks of vaccinia-SP1 were grown up in CV-1 cells without selective conditions. Vaccinia-SP1 was purified by twice banding in 36-50% w/v sucrose gradients and DNA was extracted from virions. This DNA was cut with HindIII and the resulting fragments run out on a 0.6% agarose gel. Ethidium bromide staining and UV visualisation of the DNA indicated that the 5 kb HindIII J fragment of wild-type DNA (containing the vaccinia TK gene) was absent from the recombinant vaccinia-SP1 and instead there were two new HindIII fragments, the sizes of which were consistent with the insertion into vaccinia TK of the IBV Beaudette spike sequence. Southern blotting of this agarose gel and probing with nick-translated $^{32}$P-labelled pMB179 confirmed that these new fragments did indeed contain the spike sequence.

3. Expression of IBV spike protein polypeptide in monkey kidney cells

CV-1 cells in 25 cm$^2$ bottles were infected with 40 pfu per cell of wild type or vaccinia-SP1 virus and radiolabelled between 2 and 6 hours post infection with 80 microcuries of $^{35}$S-methionine. Lysates were prepared from infected and control cells at 6 hours after infection and immunoprecipitated with rabbit anti-spike protein serum and staphylococcal protein A as described by Mackett, Smith & Moss 1985, loc. cit. The precipitated polypeptides were separated by polyacrylamide gel electrophoresis and visualised by autoradiography. In lysates prepared from vaccinia-SP1 infected cells, two high molecular weight polypeptides were specifically precipitated by anti-spike protein serum which were consistent in size with spike proteins S1 and S2 of IBV. These were absent from the cell lysates of uninfected and vaccinia wild type-infected cells. Indirect immunofluorescent antibody staining of surface fixed vaccinia-SP1 infected cells was carried out using rabbit anti-spike protein serum and fluorescein conjugated anti-rabbit serum as described by Mackett, Smith & Moss. Strong surface labelling consistent with the spike polypeptide being expressed at the cell membrane of vaccinia-SP1 infected monkey kidney cells was observed.

We claim:

1. An isolated DNA molecule which codes for an IBV spike protein polypeptide comprising a S1 or S2 polypeptide or polypeptide of S1 linked to S2.

2. A DNA molecule according to claim 1 wherein said IBV spike protein polypeptide is of IBV Beaudette, M41 or 6/82 strain.

3. A DNA molecule according to claim 2, comprising a nucleotide sequence which codes substantially only for a polypeptide selected from the group consisting of the spike protein precursor, (2) the S1 signal plus the S1 polypeptide, (3) the S1 polypeptide and (4) the S1 polypeptide plus the S2 polypeptide.

4. A DNA molecule according to claim 1, comprising a nucleotide sequence which codes substantially only for a polypeptide selected from the group consisting of (1) the spike protein precursor, (2) the S1 signal plus the S1 polypeptide, (3) the S1 polypeptide and (4) the S1 polypeptide plus the S2 polypeptide.

5. A vector carrying an inserted sequence of a DNA molecule claimed in claim 1, 2, 3 or 4.

6. A vector according to claim 5 which is a cloning vector.

7. A host incorporating a cloning vector defined in claim 6.

8. A host according to claim 7 incorporating a plasmid containing the IBV spike protein precursor cDNA, said cDNA being present in patent deposit NCIB 12101, 12102 or 12221.

9. A host according to claim 8 which is an *E. coli* bacterium.

10. A pox virus vector comprising a viral promoter sequence linked to an inserted sequence of a DNA molecule claimed in claim 1, 2, 3 or 4.

11. A vector according to claim 10 wherein the virus is fowlpox virus.

12. Mammalian cells containing a DNA molecule claimed in claim 1, 2, 3 or 4.

13. Mammalian cells containing a poxvirus vector claimed in claim 10.

* * * * *